United States Patent [19]

Wise et al.

[11] 4,128,552

[45] Dec. 5, 1978

[54] 1-[4,4-BIS(4-FLUOROPHENYL)BUTYL]-4-PHENYLTHIO-1,2,3,6-TETRAHYDROPYRIDINES AND RELATED SULFOXIDES AND SULFONES

[75] Inventors: Lawrence D. Wise, Ann Arbor, Mich.; Patrick F. Flynn, Wilmington, Del.; Glenn C. Morrison, Ann Arbor, Mich.

[73] Assignee: Warner-Lambert Company, Morris Plains, N.J.

[21] Appl. No.: 836,866

[22] Filed: Sep. 26, 1977

[51] Int. Cl.² ........................................... C07D 213/04
[52] U.S. Cl. .................................... 546/294; 424/263; 546/300; 546/302; 546/303; 546/301; 546/290
[58] Field of Search ................. 260/294.8 F, 294.8 G

[56] References Cited

U.S. PATENT DOCUMENTS

| | | | |
|---|---|---|---|
| 3,758,483 | 9/1973 | Edenhofer | 260/295 AM |
| 3,790,583 | 2/1974 | Edenhofer et al. | 260/294.8 F |
| 3,879,405 | 4/1975 | Edenhofer | 260/294.8 G |

OTHER PUBLICATIONS

Burger, Medicinal Chemistry, Second Edition, Interscience Publishers, p. 497, (1960).

*Primary Examiner*—Alan L. Rotman
*Attorney, Agent, or Firm*—Albert H. Gradis; Frank S. Chow; Anne M. Kelly

[57] ABSTRACT

Diphenylbutyltetrahydropyridines of the following formula:

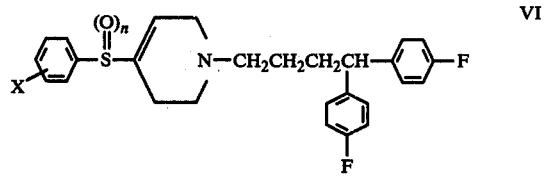

are disclosed, in which X is hydrogen, halogen such as fluorine, chlorine or bromine, trifluoromethyl, alkoxy, nitro, amino, lower alkyl of 1 to 6 carbon atoms, aryl or substituted aryl and n is 0, 1 or 2. These compounds are useful as antipsychotics.

26 Claims, No Drawings

1-[4,4-BIS(4-FLUOROPHENYL)BUTYL]-4-PHENYLTHIO-1,2,3,6-TETRAHYDROPYRIDINES AND RELATED SULFOXIDES AND SULFONES

The present invention relates to diphenylbutyltetrahydropyridines having the following structural formula:

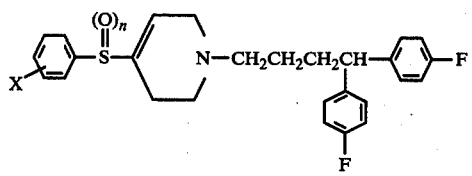

wherein X is hydrogen, halogen, trihaloloweralkyl, lower alkoxy, nitro, amino, lower alkyl, aryl or substituted aryl and n is 0, 1 or 2.

The present invention also includes within its scope the corresponding pharmaceutically acceptable acid addition salts, the quaternary ammonium salts and the N-oxides.

In the above definition for X, halogen is meant to include all four members, i.e., fluorine, chlorine, bromine and iodine. Lower alkyl and the lower alkyl portion of lower alkoxy has 1 to 6 carbon atoms as exemplified by methyl, ethyl, propyl, isopropyl and so on. Aryl is preferably a monocyclic aromatic hydrocarbon of 6 to 10 carbon atoms such as phenyl or tolyl. The aryl may be optionally substituted by groups such as the aforesaid halogen, nitro, amino, lower alkyl or lower alkoxy. The term "trihaloloweralkyl" is preferably trifluoromethyl.

The compounds of the present invention exhibit a pharmaceutical profile resembling known antipsychotics such as, for example, haloperidol or pimozide.

For example, in a test conducted in accordance with the procedure known as the Sidman Avoidance Screen, M. Sidman, Science, 118, 157 (1953), the compound of the present invention in which X is fluorine and n is 1, is active in rats at a dose of about 5 mg/kg, intraperitoneally. The compounds of this invention are further distinguished over other known antipsychotics in that they exhibit a low incidence of extrapyramidal side effects, which are undesirable side effects associated with known antipsychotics, e.g., haloperidol or pimozide.

The compounds of the invention are indicated in the management of psychotic disorders such as schizophrenia.

Generally, a dose of 5–5 mg, orally or by injection, one to three times daily is suggested.

This dosage regimen may be varied depending upon the severity of the condition and titrated according to individual needs.

The compounds of this invention are formulated into dosage forms suitable for oral administration, such as tablets and syrup, by methods well-known to the pharmacist's art. They can also be administered in the form of suppositories, which are also formulated by well-known pharmaceutical art.

For parenteral administration, the salts of the above compounds are preferable. They are formulated by dissolving the salt in water, sterilizing and packaging into individual ampules.

According to the present invention, above Compound VI is prepared by treating a starting compound of the formula:

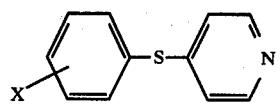

in which X is as defined hereinabove. Compound I is treated with bis(p-fluorophenyl)butyl chloride and sodium iodide to formulate a quaternary salt of the formula:

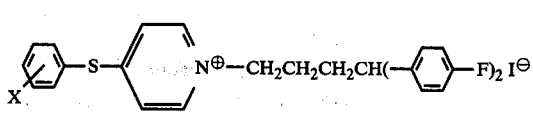

The quaternary salt, II, is reduced with a complex metal hydride, e.g., sodium or potassium borohydride to obtain a tetrahydropyridine of the formula:

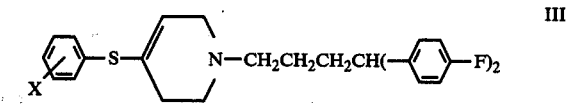

In the next step, Compound III is treated with one equivalent of an oxidizing agent to yield those compounds of this invention having the formula:

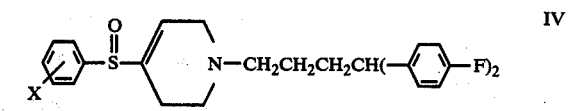

When an excess of oxidizing agent is employed, sulfones of the instant invention having the following formula result:

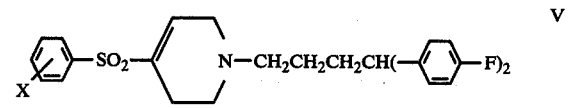

Among the oxidizing agents there may be mentioned, for example, hydrogen peroxide-acetic acid, m-chloroperbenzoic acid and so on, which are suitable for the conversion from Compound III to Compounds IV and V.

Starting Compound I above, in which X is hydrogen, is described in the Journal of American Chemical Society, Volume 59, Page 2697 (1937), whereas where X is chloro, such compound is described in Belgian Pat. No. 618,679 (1962). The disclosures in these references are incorporated herein. Other analogs of I are prepared in the same manner as described in said references and and exemplified more fully in the following examples. Temperatures given in the following examples are in degrees Centigrade.

EXAMPLE 1

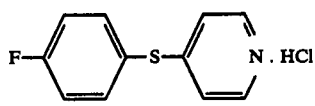 . HCl

4-[(4-Fluorophenyl)thio]pyridine hydrochloride. To 50.0g of 4-fluorobenzenethiol cooled in an ice bath at 0° was slowly added 44.3g of 4-chloropyridine. After several minutes, a vigorous reaction ensued with the formation of a white solid. The product was washed with ether and dried to yield 87.2g (92.8%) of white powder, m.p. 217°–220°. Recrystallization from isopropanol gave white needles, m.p. 224°–226°.

Anal. Calcd. for $C_{11}H_8FNS \cdot HCl$: C, 54.66; H, 3.75; Cl, 14.67; F, 7.86; N, 5.80; S, 13.27. Found: C, 54.58; H, 3.77; Cl, 14.84; F, 7.75; N, 5.77; S, 13.36.

Employing the procedure described in the above example, the following compounds were also prepared:

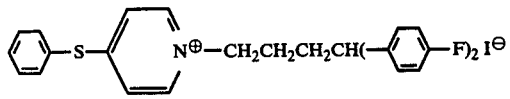

| R | Formula | Anal. | m.p. |
|---|---|---|---|
| p-F | $C_{11}F_8FNS \cdot HCl$ | CHClFNS | 224–226° |
| p-Br | $C_{11}H_8BrNS \cdot HCl$ | CHBrClNS | 233–235° |
| p-NO$_2$ | $C_{11}H_8N_2O_2S \cdot HCl$ | CHClNS | 256–258° |
| p-OCH$_3$ | $C_{12}H_{11}NOS$ | CHNS | 95–97° |
| p-CH$_3$ | $C_{12}H_{11}NS \cdot HCl$ | CHClNS | 238–240° |
| m-CF$_3$ | $C_{12}H_8F_3NS \cdot HCl$ | CHClFNS | 190–192° |
| o,o-diCl | $C_{11}H_7Cl_2NS \cdot HCl$ | CHClNS | 220–222° |
| o-Cl | $C_{11}H_8ClNS \cdot HCl$ | CHClNS | 227–229° |
| m-Cl | $C_{11}H_8ClNS \cdot HCl$ | CHClNS | 82–84° |

EXAMPLE 2

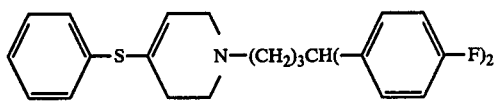

1-[4,4-Bis(4-fluorophenyl)butyl]-4-(phenylthio)-pyridinium iodide. A solution of 20.0g of 4-(phenylthio)pyridine, 60.0g of 1,1'-(4-chlorobutylidine)bis[4-fluorobenzene] and 30.4g of sodium iodide in 400 ml of acetone was refluxed for 17 hours. The resulting precipitate was collected and washed well with water. The solid was dried to afford 42.0g (68.5%) of white crystals, m.p. 217°–218.5°. Recrystallization from methanol gave an analytical sample, m.p. 219°–220°.

Anal. Calcd. for $C_{27}H_{24}F_2INS$: C, 57.97; H, 4.32; F, 6.80; I, 22.68; N, 2.50; S, 5.73. Found: C, 57.73; H, 4.34; F, 6.68; I, 22.48; N, 2.42; S, 6.08.

Employing the procedure described in the above example, the following compounds were also prepared:

| X | Formula | Anal. | m.p. |
|---|---|---|---|
| p-F | $C_{27}H_{23}F_3INS$ | CHFINS | 231–232° |
| p-Cl | $C_{27}H_{23}ClF_2INS$ | CHClFINS | 220–221° |
| p-Br | $C_{27}H_{23}BrF_2INS$ | CHBrFINS | 220–221° |
| p-NO$_2$ | $C_{27}H_{23}F_2IN_2O_2S$ | CHFINS | 204–205° |
| p-OCH$_3$ | $C_{28}H_{26}F_2INOS$ | CHFINS | 206–207° |
| p-CH$_3$ | $C_{28}H_{26}F_2INS$ | CHFINS | 213–214° |
| m-CF$_3$ | $C_{28}H_{23}F_5INS$ | CHFINS | 202–203° |
| o,o-diCl | $C_{27}H_{22}Cl_2F_2INS$ | CHClFINS | 124–126° |
| m-Cl | $C_{27}H_{23}ClF_2INS$ | CHClFINS | 205–206° |

EXAMPLE 3

1-[4,4-Bis(4-fluorophenyl)butyl]-1,2,3,6-tetrahydro-4-(phenylthio) pyridine hydrochloride. To a stirred suspension of 14.0g of 1-[4,4-bis(4-fluorophenyl)butyl]-4-(phenylthio)pyridinium iodide in 500 ml of methanol at room temperature was added 2.28g of sodium borohydride potionwise over 15 minutes. The resulting clear solution was allowed to stir for an additional hour after which the solvent was evaporated. To the residue was added a saturate sodium carbonate solution. The mixture was extracted with methylene chloride. The organic extracts were dried over anhydrous sodium sulfate and evaporated. The residual oil was treated with anhydrous ethanolic hydrogen chloride to give 10.9g (92.0% of white powder, m.p. 165°–166°.

Anal. Calcd. for $C_{27}H_{27}F_2NS \cdot HCl$: C, 68.70; H, 5.98; Cl, 7.51; F, 8.05; N, 2.97; S, 6.79. Found: C, 68.45; H, 6.03; Cl, 7.59, F, 8.09; N, 2.78; S, 6.88.

Employing the procedure described in the above example, the following compounds were also prepared:

| X | Formula | Anal. | m.p. |
|---|---|---|---|
| p-F | $C_{27}H_{26}F_3NS \cdot HCl$ | CHClFNS | 138–139° |
| p-Cl | $C_{27}H_{26}ClF_2NS \cdot HCl$ | CHClFNS | 146–147° |
| p-Br | $C_{27}H_{26}BrF_2NS \cdot HCl$ | CHBrClFNS | 145–146° |
| p-NO$_2$ | $C_{27}H_{26}F_2N_2O_2S$ | CHFNS | 88–89° |
| p-OCH$_3$ | $C_{28}H_{29}F_2NOS \cdot C_4H_6O_6$ | CHFNS | 139–141° |
| p-CH$_3$ | $C_{28}H_{29}F_2NS \cdot HCl$ | CHClFNS | 152–154° |
| m-CF$_3$ | $C_{28}H_{26}F_5NS \cdot C_4H_6O_6$ | CHFNS | 143–144° |
| o,o-diCl | $C_{27}H_{25}Cl_2F_2NS \cdot HCl$ | CHClFNS | 139–140° |
| o-Cl | $C_{27}H_{26}ClF_2NS \cdot HCl$ | CHClFNS | 165–166° |
| m-Cl | $C_{27}H_{26}ClF_2NS \cdot HCl$ | CHClFNS | 147–148° |

EXAMPLE 4

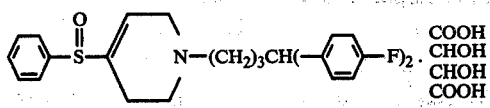

1-[4,4-Bis(4-fluorophenyl)butyl]-1,2,3,6-tetrahydro-4-(phenylsulfinyl)-pyridine 2,3-dihydroxybutanedioate. A solution of 11.0g of 1-[4,4-bis-4-(fluorophenyl)butyl]-1,2,3,6-tetrahydro-4-(phenylthio) pyridine hydrochloride and 2.64g of 30% hydrogen peroxide in 100ml of acetic acid was allowed to stand at room temperature for four days. The acetic acid was removed in vacuo, and the residue neutralized with 1N sodium hydroxide. Extraction of the product into chloroform followed by evaporation yielded a light brown oil. The d, l-tartrate salt was generated in and recrystallized from methanol to afford a white powder, m.p. 162°–163°.

Anal. Calcd. for $C_{27}H_{27}F_2NOS \cdot C_4H_6O_6$: C, 61.86; H, 5.53; F, 6.32; N, 2.33; S, 5.33. Found: C, 61.65; H, 5.55; F, 6.39, N, 2.39; S, 5.50.

Empolying the procedure described in the above example, the following compounds were also prepared:

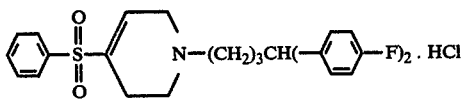

| X | Formula | Anal. | m.p. |
|---|---|---|---|
| p-F | $C_{27}H_{26}F_3NOS \cdot C_4H_6O_6$ | CHFNS | 177–178° |
| p-Cl | $C_{27}H_{26}ClF_2NOS \cdot C_4H_6O_6$ | CHClFNS | 166–168° |
| p-Br | $C_{27}H_{26}BrF_2NOS \cdot C_4H_6O_6$ | CHBrFNS | 156–157° |
| p-NO$_2$ | $C_{27}H_{26}F_2N_2O_3S \cdot C_4H_6O_6$ | CHFNS | 163–164° |
| p-OCH$_3$ | $C_{28}H_{29}F_2NO_2S$ | CHFNS | 127–129° |
| p-CH$_3$ | $C_{28}H_{29}F_2NOS \cdot C_4H_6O_6$ | CHFNS | 162–163° dec |
| m-CF$_3$ | $C_{28}H_{26}F_5NOS \cdot C_2H_2O_4$ | CHENS | 139–140° dec |
| o,o-diCl | $C_{27}H_{26}ClF_2NOS$ | CHClFNS | 136–165° |
| o-Cl | $C_{27}H_{26}ClF_2NOS$ | CHClFNS | 163–165° |
| m-Cl | $C_{27}H_{26}ClF_2NOS \cdot C_4H_6O_6$ | CHClFNS | 126–128° |

EXAMPLE 5

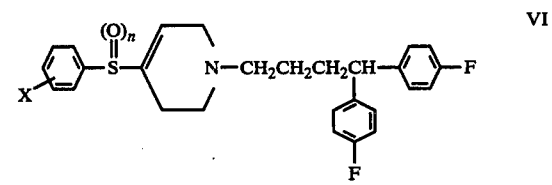

1-[4,4-Bis(4-fluorophenyl)butyl]-1,2,3,6-tetrahydro-4-(phenylsulfonyl)-pyridine hydrochloride. A solution of 7.60g of 1-[4,4-bis(4-fluorophenyl)-butyl]-1,2,3,6-tetrahydro-4-(phenylthio)pyridine hydrochloride and 18.7g of 30% hydrogen peroxide in 100ml of acetic acid was allowed to stand at room temperature for 3 days. The reaction solution was neutralized at 0° with 50% sodium hydroxide, and the product was extracted into chloroform. The organic extracts were charcoaled and filtered through a bed of florisil. Evaporation of the solvent gave a thick oil. The hydrochloride was formed in ether to give a light tan powder, m.p. 211°–212° dec.

Anal. Calcd. for $C_{27}H_{27}F_2NO_2S \cdot HCl$: C, 64.34; H, 5.60; Cl, 7.03; F, 7.54; N, 2.78; S, 6.36. Found: C, 64.30; H, 5.81; Cl, 6.82; F, 7.49; N, 2.81; S, 6.49.

Employing the procedure described in the above example, the following compounds were also prepared:

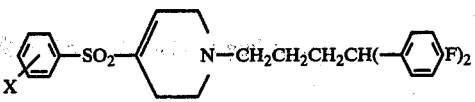

| X | Formula | Anal. | m.p. |
|---|---|---|---|
| p-F | $C_{26}H_{25}F_3NO_2S \cdot HCl$ | CHClFNS | 194–195° |
| p-Cl | $C_{27}H_{26}ClF_2NO_2S \cdot HCl$ | CHClFNS | 150–152° |
| p-Br | $C_{27}H_{26}BrF_2NO_2S$ | CHBrFNS | 141–142° |
| p-NO$_2$ | $C_{27}H_{26}F_2N_2O_4S \cdot HCl$ | CHClFNS | 194–195° |
| p-CH$_3$ | $C_{28}H_{29}F_2NO_2S \cdot HCl$ | CHClFNS | 147–148° |
| m-CF$_3$ | $C_{28}H_{26}F_5NO_2S \cdot C_4H_6O_6$ | CHFNS | 156–157° dec |
| m-Cl | $C_{27}H_{26}ClF_2NO_2S$ | CHClFNS | 83–85° |

We claim:

1. A compound of the formula:

VI in which X is hydrogen, halogen, trifluoromethyl, lower alkoxy, aryl of 6 to 10 carbon atoms, lower alkyl, nitro or amino n is 0, 1 or 2 and the corresponding pharmaceutically acceptable acid addition salts thereof.

2. A compound according to claim 1 in which X is hydrogen and n is 2 and its hydrochloride salt.

3. A compound according to claim 1 in which X is parafluoro and n is 2.

4. A compound according to claim 1 wherein X is parachloro and n is 2.

5. A compound according to claim 1 in which X is parabromo and n is 2.

6. A compound according to claim 1 in which X is paranitro and n is 2.

7. A compound according to claim 1 in which X is paramethyl and n is 2.

8. A compound according to claim 1 in which X is metatrifluoromethyl and n is 2.

9. A compound according to claim 1 in which X is hydrogen and n is 1.

10. A compound according to claim 1 in which X is parafluoro and n is 1.

11. A compound according to claim 1 in which X is bromo and n is 1.

12. A compound according to claim 1 in which X is nitro and n is 1.

13. A compound according to claim 1 in which X is paramethoxy and n is 1.

14. A compound according to claim 1 in which X is methyl and n is 1.

15. A compound according to claim 1 in which X is metatrifluoromethyl and n is 1.

16. A compound according to claim 1 in which X is ortho, ortho-dichloro and n is 1.

17. A compound according to claim 1 in which X is hydrogen and n is 0.

18. A compound according to claim 1 in which X is parafluoro and n is 0.

19. A compound according to claim 1 in which X is parachloro and n is 0.

20. A compound according to claim 1 in which X is parabromo and n is 0.

21. A compound according to claim 1 in which X is paranitro and n is 0.

22. A compound according to claim 1 in which X is paramethoxy and n is 0.

23. A compound according to claim 1 in which X is paramethyl and n is 0.

24. A compound according to claim 1 in which X is metatrifluoromethyl and n is 0.

25. A compound according to claim 1 in which X is ortho, ortho-dichloro and n is 0.

26. A compound of the formula II:

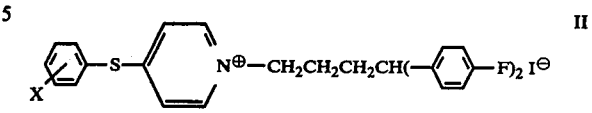

in which X is hydrogen, halogen, trifluoromethyl, lower alkoxy, aryl of 6 to 10 carbon atoms, lower alkyl, nitro, or amino.

* * * * *